United States Patent [19]

Hrebeniuk

[11] Patent Number: Plant 6,104

[45] Date of Patent: Feb. 9, 1988

[54] POINSETTIA PLANT—H-183

[76] Inventor: Alexander Hrebeniuk, R.D. 1, Box 118, Sugar Run, Pa. 18846

[21] Appl. No.: 766,547

[22] Filed: Aug. 19, 1985

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Joseph W. Molasky

[57] ABSTRACT

A poinsettia plant of medium size and compact habit which produces very dark red blooms with blue toning and tight centers. The stems are strong and heavy and the foliage is uniquely characterized by an ability to retain its original propagation leaves and resist the burnt edge appearance which is emdemic to other species.

1 Drawing Figure

This invention relates to a new species of poinsettia plant which bears my code H-183 and which is known botanically as *Euphorbia pulcherrima.*

This new species is the result of a controlled cross between the seed parent of U.S. Plant Pat. No. 4,434 and a seedling of the pollen parent which is available commercially as Eckespoint C-1.

This new species or cultivar was asexually reproduced from cuttings in my greenhouses at Sugar Run, Pa. and it has retained its distinctive characteristics through successive propagations.

It is an object of this invention to provide a new and uniquely attractive variety of poinsettia plant which is suitable for pot growth production and which is characterized by a compact habit, a resistance to "dark spotting" when watered and a resistance to fade with changes in temperature.

One advantageous feature of this new cultivar is its ability to grow at relatively cool temperatures of about 60°–62° F. When fully bloomed this cultivar will retain its flowers for about three months when held at temperatures of about 60° F.

The following characteristics distinguish this new cultivar from its seed parent, its pollen-parent and other poinsettias in the floriculture industry:

(1) This new cultivar exhibits a self-branching ability which surpasses that of the Eckespoint C-1 variety.

(2) A second characteristic is the ability of my new cultivar to retain its foliage for a period longer than that of the Eckespoint C-1 variety and for at least as long as the variety described by Annette Hagg in U.S. Plant Pat. No. 2,962.

(3) This new cultivar is an early blooming variety which is grown at about 60°–62° F. and it produces saleable blooms by about mid-November. The blooms are a dark red with much blue toning and they are very attractive. They are medium sized with tight centers.

(4) The foliage is deep green with a dark bluish tinge and the leaves are medium size. On single stem plants this foliage is essentially heart shaped but on branched plants the foliage has a somewhat serrated appearance.

(5) A commercially attractive feature of this cultivar is its ability to retain its foliage for extended periods including the original propagation leaves. The original leaves not only remain on the plant but they retain their original appearance and they are not susceptible to the burnt edge disease which inflicts other varieties.

(6) This new cultivar reproduces easily and the cuttings take root very rapidly. The rate of growth has a tendency to decline as the lateral shoots increase in number and size but this can be alleviated by pruning.

(7) During propagation there is a tendency for atmospheric moisture to bead up and form water droplets on the foliage to a greater extent than is seen on other varieties of poinsettia plants. This suggests that the foliage exudes a waxy film which contributes to its ability to withstand wilting to a greater degree than other varieties.

The accompanying photograph depicts a typical specimen of my new cultivar with colors as true to the original as photographic methods will allow. The color references in the following description corresponds to Code Nos. in The Royal Horticultural Society Colour Chart except when general color terminology is employed in which event the colors are described by reference to common dictionary definitions.

The following description reports on specimens asexually reproduced under my diretion at greenhouses in Sugar Run, Pa.

Parentage: Seedling.

*Seed parent.*—A selected red seedling (H-L1) of U.S. Plant Pat. No. 4,434.

*Pollen parent.*—A selected red seedling of the cultivar Eckespoint C-1 variety.

Growth habit: Upright growth of medium size suitable for pot culture. Branching is superior to that of the Eckespoint C-1 variety. The stems are strong and heavy.

Blooming: An early eight week variety which follows essentially the blooming habit of the cultivar Eckespoint C-1 variety and which is saleable by mid-November.

Temperature: This new poinsettia plant is grown at temperatures of 60°–62° F. The plant can be maintained and held indoors for extended periods at temperatures of from about 70°–75° F.

Foliage: Medium sized leaves of green and dark blue. In single stem plants the leaves are somewhat heart-shaped but in branched plants the leaves have some serration. The original propagation leaves remain on the plant and do not become burned along the edges. Foliage retention is superior to that of the Eckespoint (Continued on next page.)

C-1 variety and equal to that of the Hegg varieties. During propagation there is a tendency for mist to bead up and remain on the foliage to a greater extent than on other varieties, a characteristic which is typical of foliage having a waxy film. The foliage is hardy and does not wilt readily during propagation. The leaf color on mature leaves is forest green (Code No. 147A) on the upper side and meadow green (Code No. 147B) on the underside. The petiole is red (Code No. 53A). The leaves are spaced about the plant with up to 10 leaves per stem. Fully grown leaves are about 10 cm wide and 16 cm long, the upper side being smooth and the underside having a rough texture.

Flowers (cyathia): Vary dark red on both sides with much blue toning. They are generally pointed in shape and borne at various angles to the stem.

*Quantity.*—The number of blooms per stem range from about 4 to 6. The stamens are light green; the styles are light green; the pollen a golden yellow; and the ovaries a light orange.

*Texture.*—The upperside has a flat texture and the underside has a generally smooth texture.

*Bracts.*—The bracts are the size and shap of leaves. A typical full grown bract measures about 9 cm in width and 16 cm in length. The color on the upper side is red (Code No. 53B) and the underside is light red (Code No. 53C). In a typical plant each stem contains up to about 26 bracts and a full bloom measures about 14 inches across.

Stems and reproduction: The new wood is dark gray and becomes dark greenish red as the wood ages. The strong and heavy stems are characterized by a bark which is smooth when new and which becomes rough with aging.

I claim:

1. A new and distinct variety of poinsettia plant substantially as illustrated and described and characterized as to novelty by its upright medium size growth with vigorous self branching and very dark red blooms with blue toning and tight centers; medium size green foliage with dark bluish tones characterized by an ability to retain its color without a burnt edge appearance; the original propagation leaves remain on the plant and the stems are strong and heavy; uniform rooting with an abundance of cuttings which root rapidly; it has an ability to maintain its beauty and life over extended periods at a temperature in the range of 60° to 62° F.

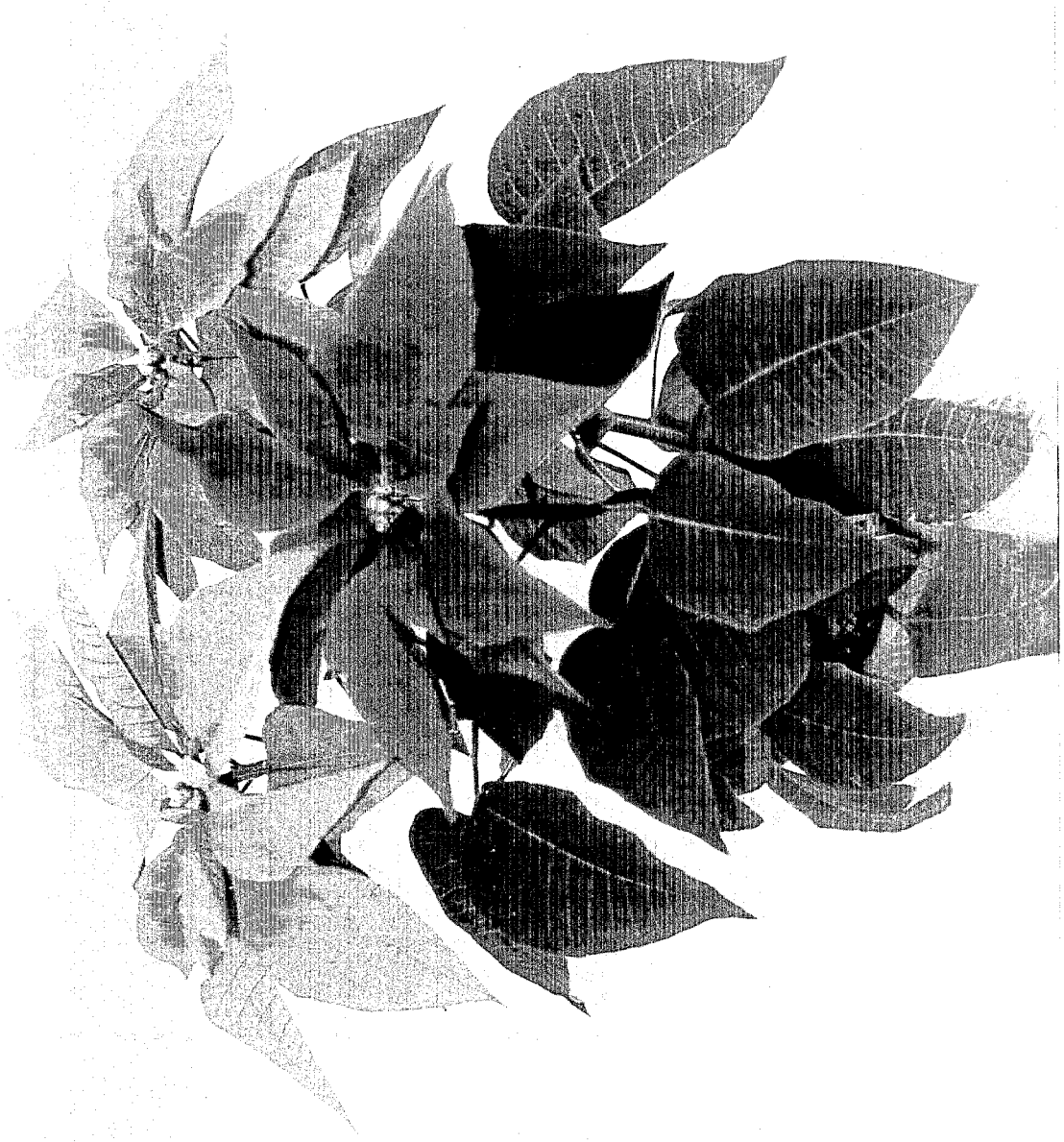

* * * * *